United States Patent [19]

Bent

[11] 4,109,735
[45] Aug. 29, 1978

[54] ROTARY SURGICAL DRIVER

[75] Inventor: John H. Bent, Carpenteria, Calif.

[73] Assignee: Minnesota Mining and Manufacturing Company, St. Paul, Minn.

[21] Appl. No.: 710,784

[22] Filed: Aug. 2, 1976

Related U.S. Application Data

[63] Continuation of Ser. No. 541,197, Jan. 15, 1975, abandoned, which is a continuation-in-part of Ser. No. 366,316, Jun. 4, 1973, abandoned.

[51] Int. Cl.² ............................................. A61B 17/18
[52] U.S. Cl. .............................. 173/163; 128/92 EC; 137/625.69; 173/169
[58] Field of Search ............. 128/92 EK, 92 G, 92 R, 128/305; 32/DIG. 1; 173/163, 169; 137/625.69; 91/426

[56] References Cited

U.S. PATENT DOCUMENTS

| 2,010,210 | 8/1935 | Witt | 279/82 |
| 2,702,047 | 2/1955 | Seeloff | 137/625.69 |
| 2,946,315 | 7/1960 | Doeden | 173/163 X |
| 3,093,360 | 8/1935 | Krouse | 173/169 |
| 3,718,340 | 2/1973 | Stewart | 128/92 EC |

Primary Examiner—Ernest R. Purser
Assistant Examiner—William F. Pate, III
Attorney, Agent, or Firm—Cruzan Alexander; Donald M. Sell; Edward T. Okubo

[57] ABSTRACT

A driver including a hand piece adapted to be held in the hand of a user, an air motor mounted within the hand piece, and a barrel coupled transversely to the hand piece. A medical instrument is rotatably mounted in the barrel and releasably retained therein by a releasable detent located to the rear of the barrel. Air flow to the air motor is controlled by a valve having a trigger-like operating member. The direction of rotation of the air motor is controlled by a manually operable reversing valve.

5 Claims, 7 Drawing Figures

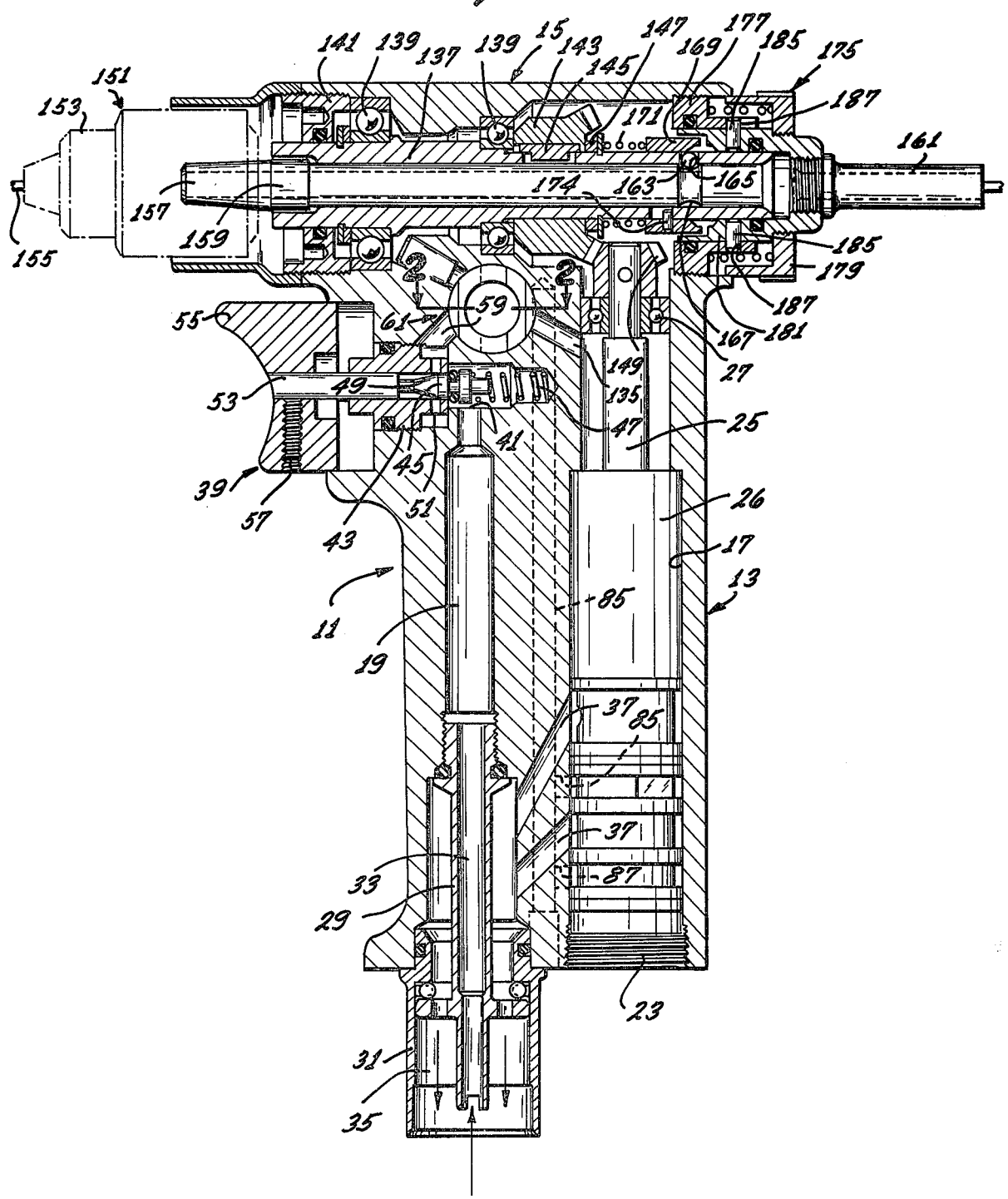

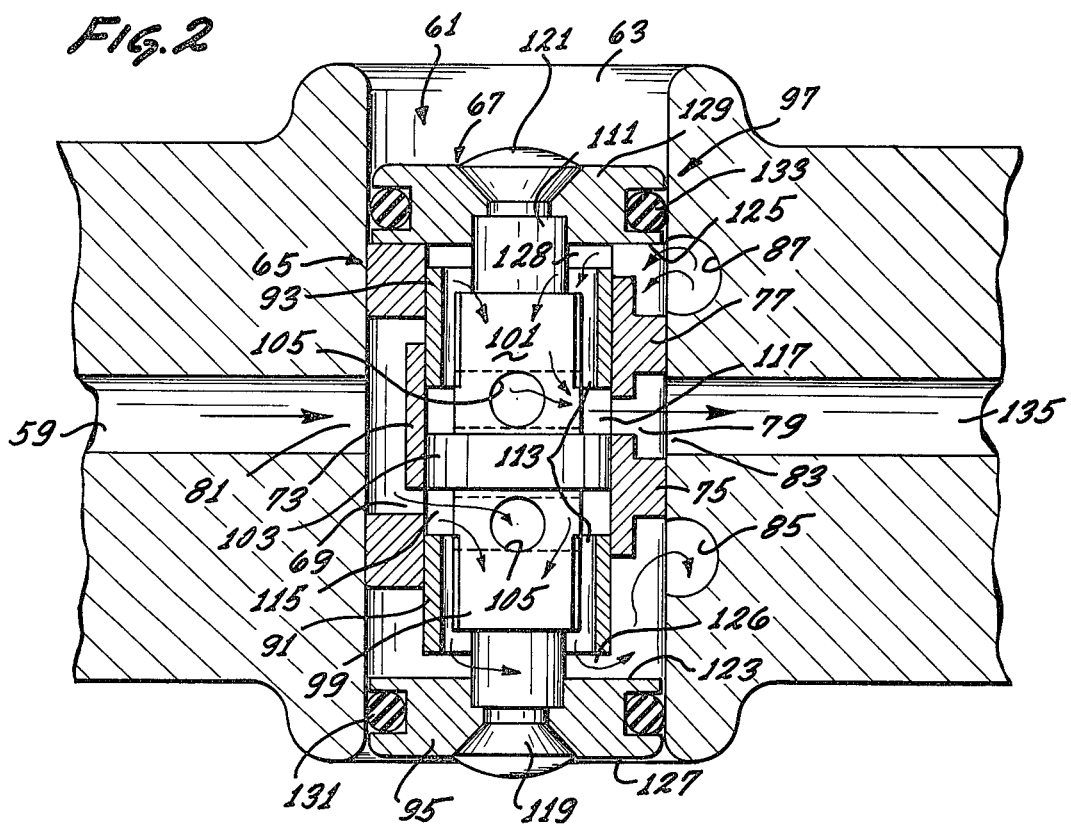
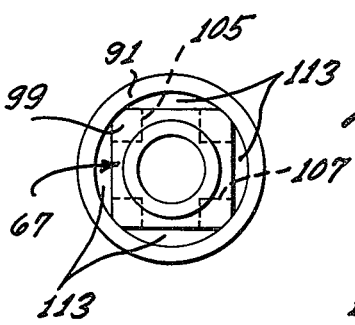
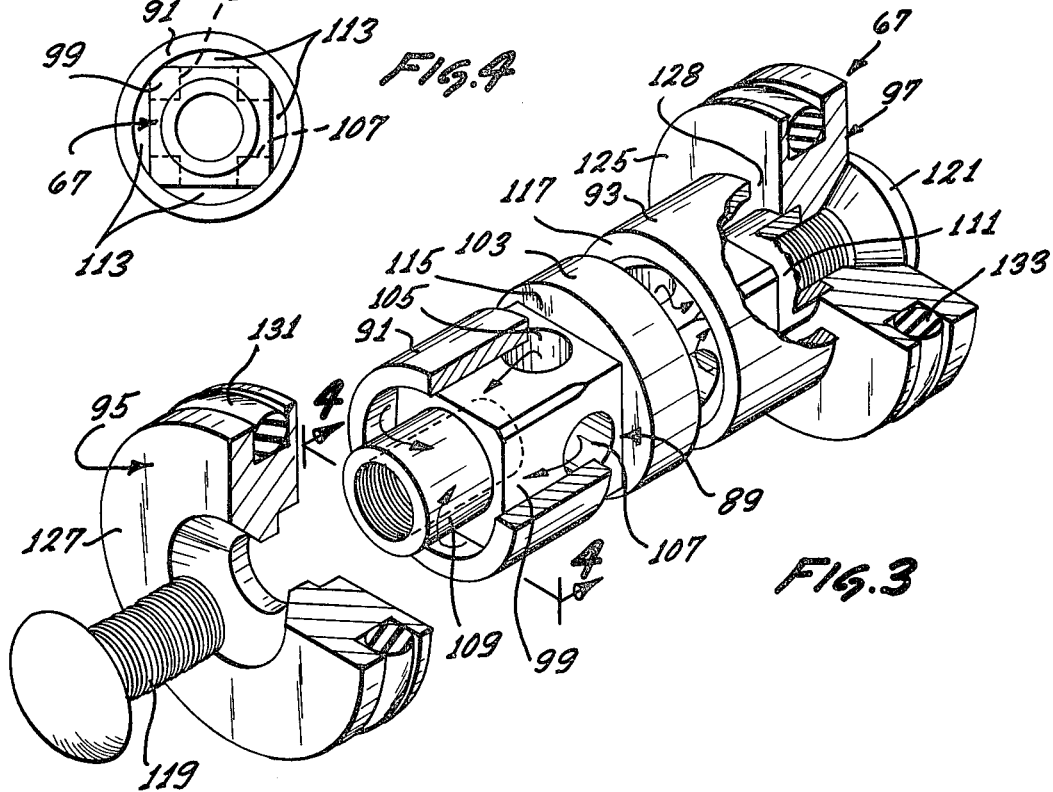

ROTARY SURGICAL DRIVER

This is continuation of Ser. No. 541,197, filed 1/15/75, abandoned, which is a continuation-in-part of application Ser. No. 366,316, filed on June 4, 1973, abandoned.

BACKGROUND OF THE INVENTION

Various work operations require that a part or member be rotated with precision. In the medical field such a function is commonly carried out by a driver which should be capable of receiving several different types of instruments. A driver is used, for example, in surgery to drill a hole in a bone and to drive a wire into portions of a bone separated by a fracture.

Normally in the use of the driver as a power source for surgical procedures, the power source should have sufficient versatility to be usable with different types of instruments. For example, when used with a wire driving instrument, several different instruments may be used in one procedure because of the need to use wires of different size. Thus, instruments must be changed quickly and mounted properly for accurate driving. In any surgical procedure in which the patient is under anesthesia, the surgeon prefers to complete the procedure quickly since the length of time under anesthesia should be reduced, if possible. Where time is consumed during a procedure due solely to the time needed to change instruments by use of separate key locking members, or relatively complex manipulations, there is objection. Moreover, the surgical procedure sometimes results in fluids contacting the driver or the instruments or both so that it is difficult to turn elements on the driver or instrument for the purpose of adjust or change of instruments.

For example, a driver having a round handle may tend to slip if the surgeon's gloves are wet. Slippage because of wet gloves may also render more difficult the task of changing instruments.

One of the more practical problems to provide a driver which may be used with a wire driving instrument, that is, a tool used as a power source to rotate an instrument which engages a wire to be driven into bone structure as is frequently performed during osteological procedures. The same driver may later be used in a different procedure, e.g. a skull puncture. In wire driving, the length of wire may vary, in some instances the wire may be as long as 15 to 20 centimeters. Thus, the driver itself must be capable of receiving such a wire, while still achieving the objective of compatibility with other instruments which must be accurately aligned, securely held and properly driven. Any "wobble" of the driven instrument must be avoided.

Due to the versatility needed in such a driver, the release mechanism which must be actuated to change instruments should be easily operated, but not positioned in such a location that it may be accidentally actuated to release an instrument during a surgical procedure.

A driver typically includes a handle or hand piece which is adapted to be manually grasped and a barrel which extends transverse to the handle. The barrel typically contains the air motor and a rotatable member such as a chuck.

One problem with this construction is that for wire drilling, the barrel should be open so that the wire can be fed through it from the rear to the front. This creates a problem when the air motor is mounted within the barrel. One prior art driver employs an air motor in the handle but this driver is foot controlled and the air motor is removable from the handle.

Any driver which is foot controlled is subject to the criticism that it limits the mobility of the surgeon, i.e. the surgeon must always stand close to the foot switch and if the surgeon must move away from the switch, for some reason, the switch must be located before the procedure can be resumed. A driver with a pistol grip control overcomes this disadvantage. Where such a tool also permits considerable versatility, to the extent of receiving a wire driving instrument, and easy interchange of instruments, a truly unique surgical power source is provided.

DESCRIPTION OF THE PRIOR ART

Gas operated drivers for surgical use are known, especially in wire driving in which the unit is controlled by a foot pedal. The unit includes a hand piece, which is a separate piece of equipment, and which is attached to a motor. The hand piece is of a round and of generally tubular configuration. The foot switch is used to control operation and speed.

U.S. Pat. No. 3,718,340 of Feb. 27, 1973 describes a drill chuck for surgical use. An electric motor is positioned in a generally round handle, control of the unit apparently being from a remote position. The use of an electric motor, even if explosion proof, is objectionable as well as the remote control feature.

U.S. Pat. No. 3,428,327 of Feb. 18, 1969, describes an air driven tool in which the motor is in the barrel or transverse to the handle. A pistol grip type of control is described. Such a tool cannot accept long lengths of wires because of the motor location, and includes a collar at the forward end which slides rearwardly over a barrel housing forward of a gear and clutch assembly.

U.S. Pat. No. 3,635,605 of Jan. 18, 1972, a reversible gas operated driver in which the motor is located transversely of the handle and a trigger control which is operative in one position to turn the motor forward and in another position to reverse the motor direction.

U.S. Pat. No. 3,093,360 of June 11, 1963, relates to a gas operated tool with the motor transverse to the handle, a pistol grip motor actuation and a reverse mechanism located to the rear of the motor.

In the above prior art devices, where the motor is located transversely to the handle, the unit cannot accept wire driving instruments due to the position of the motor. Moreover, any member assembled to such tools is normally supported at one end rather than at two spaced locations. Those units described as surgical tools have remote control rather than pistol grip type of control, a definite disadvantage for hand held surgical tools.

SUMMARY OF THE INVENTION

The present invention provides a driver which is adapted to perform many different precision operations in surgical procedures including drilling and wire driving. The air motor is permanently mounted within the handle so that it does not interfere with the wire driving operation. The driver is driven by air supplied to the air motor through passages in the handle. The handle is structured so that it does not rotate in the user's hand, even though wet. Control means for turning the air motor on and off is provided in the handle. The control means includes an operating member mounted for sliding movement on the handle in a position to be operated by the index finger of the user much in the same manner as a trigger on a handgun.

It is desirable to be able to reverse the direction of rotation of the air motor. Reversing the air motor allows, for example, removal of screws or wires previously screwed or driven into a bone. To accomplish this, a reversing valve is used to reverse the direction of air flow through the air motor.

The present invention provides a reversing valve having forward and reverse positions for causing the air motor to be driven in the forward and reverse directions, respectively. The reversing valve can be manually moved between the forward and reverse positions thereof.

One feature of the reversing valve is that it is retained by the air being supplied to the air motor in the forward and reverse positions, depending upon which of these positions it is manually placed in. This retention of the reversing valve in the forward and reverse positions substantially reduces or eliminates the danger of inadvertent reversal of the motor by the operator. Obviously, an inadvertent reversal of the air motor during surgery could be most detrimental.

The reversing valve can advantageously be mounted in a chamber in the handle of the driver. The reversing valve may include a sleeve fixed within the chamber and a valve element slidable in the sleeve between the forward and reverse positions. To facilitate manual movement of the valve element, the opposite ends of the chamber are preferably open so that the valve element can be directly engaged and driven by the hand of the operator.

The driver provides a supply conduit for supplying air at supply pressure to the reversing valve and an exhaust conduit extending from the reversing valve to a suitable exhaust outlet. The driver also includes first and second conduit sections each of which leads from the reversing valve to the air motor. When the valve element is placed in the forward position, it provides communication between the supply conduit and the first conduit section and between the second conduit section and the exhaust conduit to thereby cause the air motor to be driven in the forward direction.

The reversing valve includes first and second pistons having inner faces. When the valve element is on the forward side of a null position, air acts on the first of these faces to tend to force the valve element toward the forward position. Conversely, when the valve element is on the reverse side of the null position, it forces the valve element to the reverse position. Accordingly, the valve element is automatically biased toward the forward and reverse positions, depending upon which side of the null position the valve element is placed in.

To facilitate construction of one of the passages in the valve element, the valve element includes a sleeve and a core member. Portions of the inner periphery of the sleeve and the outer periphery of the core member are spaced from each other to partially define such passage.

The driver rotates a driven member or a tool such as an instrument for surgical procedures. Different instruments are required for wire driving and for driving screws and other functions. The driver of this invention has means for facilitating rapid replacement of instruments or other driven members which generally include a shank supported within the driver at one end and a driving connection at the other end thereby supporting the instrument at spaced points. Specifically, a driven member is released by rotating an operating member and, once released, it can be easily manually removed Moreover, the driver of this invention may be sterilized by gas or by autoclave.

The invention can best be understood by reference to the following description taken in connection with the accompanying illustrative drawings.

BRIEF DESCRIPTION OF THE DRAWINGS

FIG. 1 is a sectional view through a driver constructed in accordance with the teachings of this invention;

FIG. 2 is an enlarged fragmentary sectional view taken generally along line 2—2 of FIG. 1 and showing the reversing valve;

FIG. 3 is a partially exploded perspective view of the valve element of the reversing valve;

FIG. 4 is an elevational view taken generally along line 4—4 of FIG. 3;

DESCRIPTION OF THE PREFERRED EMBODIMENT

Figure 5:
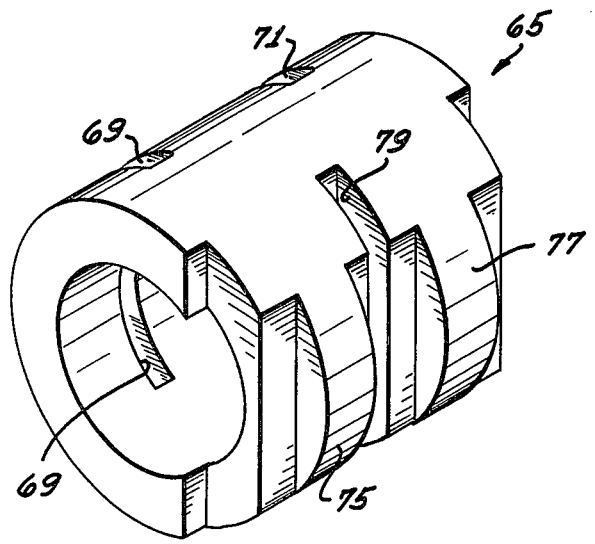
FIG. 5 is a perspective view of one side of the sleeve of the reversing valve.

FIG. 1 shows a driver 11 including a handle 13 adapted to be held in one hand of the operator and a barrel 15 which may be integral with the handle. The handle 13 has stepped parallel bores 17 and 19 formed therein, each of which extends upwardly from the bottom of the handle 13. The handle is roughly two inches across, as seen in FIG. 1 and roughly one inch thick. This generally rectangular handle assists in preventing the tool from turning in the hand of the user, especially if a sideways force must be applied. As will be appreciated, the corners and edges of the handle are rounded for comfort but the overall configuration of the handle is rectangular in the sense that it is wider than it is thick and includes a contour to locate the hand properly along the handle. The "feel" of the handle is important in surgical procedures in which the surgeon's hand is the principal guide in the position of the tool which is generally accurately controlled manually by the surgeon.

An air motor 21 is mounted in the bore 17 and retained therein by a retainer 23 which is threaded into the lower end of the bore 17. The air motor may be of any type which is suitable for driving tools. By way of example, the air motor shown in applicant's U.S. Pat. No. 3,238,848 may be employed in the driver 11. The air motor 21 drives an output shaft 25 through a bearing and gear assembly which is shown diagrammatically in FIG. 1. The shaft 25 is mounted for rotation in any suitable manner such as by the assembly 26 and one or more bearings 27.

A tube 29 is coaxially mounted within the bore 19 by screw threads. A short larger diameter tube 31 is suitably mounted in the bore 19 in coaxial relationship therewith. The tube 29 defines an air inlet passage 33. The bore 19, the tube 29, and the tube 31 define an annular exhaust passage 35. One or more exhaust passages 37 (two being illustrated in FIG. 1) lead from the air motor to the exhaust passage 35. The outer or lower regions of the tubes 29 and 31 form a connector which is adapted for connection to a coaxial conduit (not shown) which supplies air at a predetermined supply pressure for driving the motor 21 and which delivers the exhaust air to a suitable exhaust outlet (not shown).

Air at supply pressure sufficient to drive the air motor 21 is supplied from the inlet passage 33 through the upper portion of the bore 19 to a control valve 39 which is located in the handle 13. The control valve 39 controls the flow of air to the air motor 21, and therefore can be operated to turn the motor on and off. Preferably the control valve 39 is a metering valve so that the speed of the air motor 21 can be controlled by the degree to which the control valve 39 is open.

The handle 13 has a transverse, stepped bore 41 opening along one longitudinal face of the handle. A threaded bushing 43 is threaded into the bore 41. A valve element 45 is mounted in the bushing 43 for sliding movement. The valve element is biased to the left toward a closed position by a spring 47. The valve element 45 has a tapered section 49 which allows it to meter air flow through the control valve 39.

In the position shown in FIG. 1, the control valve 39 is in a normal or closed position. To open the control valve 39, the valve element 45 is moved to the right against the biasing force of the spring 47 to allow the tapered section 49 to provide communication between the bore 19 and radial ports 51 in the bushing 43. By moving the valve element 45 further to the right as viewed in FIG. 1, the restriction imposed by the valve element is progressively reduced to thereby increase air flow to the ports 51 and to the air motor 21.

The valve element 45 has a stem section 53 which is connected to an operating member 55 in any suitable manner such as by a set screw 57. The operating member 55 is mounted for sliding movement in the outer section of the bore 41. When the handle 13 is grasped by the hand of the user, the operating member 55 can be moved inwardly, i.e., to the right as viewed in FIG. 1, against the biasing action of the spring 47 by the index finger. Thus, the operating member 55 is trigger-like in relation to the handle 13 and the barrel 15.

Supply air from the ports 51 enters a passage 59 which forms an air inlet to a reversing valve 61 (FIGS. 1 and 2). The reversing valve controls the direction of rotation of the air motor 21 and hence the direction of rotation of the output shaft 25.

The reversing valve 61 is mounted in an open ended cylindrical chamber 63 (FIG. 2) in the handle 13. The axis of the chamber 63 extends transversely to the axis of the handle and to the axis of the bore 41. The reversing valve 61 includes a sleeve 65 (FIGS. 2, 5 and 6) and a valve element 67 (FIGS. 2-4) mounted for sliding movement in the sleeve 65 and in the chamber 63.

Figure 6:
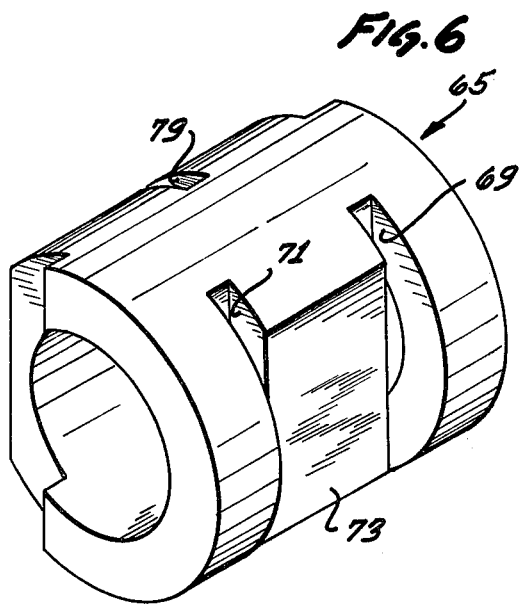
FIG. 6 is a perspective view of the other side of the sleeve of the reversing valve.

The sleeve 65 is suitably fixedly mounted within the chamber 63. The sleeve 65 is cylindrical except that portions thereof have been removed to define or partially define ports or passages. With reference to FIGS. 2, 5 and 6, the sleeve 65 has inlet slots or apertures 69 and 71. The inlet apertures 69 and 71 are separated by a wall section 73, the outer surface of which is substantially planar as shown in FIG. 6.

The sleeve 65 also had lands 75 and 77 separated by an exhaust slot or aperture 79. Portions of the sleeve 65 axially outwardly of the lands 75 and 77 are cut away as best shown in FIG. 5.

The inlet apertures 69 and 71 communicate with a supply port 81 (FIG. 2) and the exhaust aperture 79 communicates with an exhaust port 83. The portions of the chamber 63 axially outwardly of the lands 75 and 77, respectively, communicate with conduit sections 85 and 87, respectively. The conduit sections 85 and 87 lead to the air motor 21.

The valve element 67 generally includes a core 89, a pair of sleeves 91 and 93, and a pair of pistons 95 and 97. The core 89, which may be integrally constructed, includes a pair of identical block sections 99 and 101 of generally square cross sectional configuration and a cylindrical wall section 103 which separates the block sections. Each of the block sections 99 and 101 has passages 105 and 107 extending completely therethrough as best shown in FIG. 4. The opposite ends of the core 89 are defined by internally threaded nut sections 109 and 111, respectively.

In the embodiment illustrated, the inner periphery of the sleeve 91 is generally cylindrical (FIG. 4) whereas the outer periphery of the block 99 is generally square. The sleeve 91 is attached to the block section 99 in any suitable manner such as by a press fit. This leaves four clearance spaces or passage sections 113 between the sleeve 91 and the block 99.

The sleeve 93 and the block section 101 are identical to the sleeve 91 and the block section 99, respectively. Each of the sleeves 91 and 93 is axially spaced from the wall section 103 to define annular spaces 115 and 117, respectively.

The pistons 95 and 97 are mounted on the nut sections 109 and 111, respectively. The pistons 95 and 97 are retained on the nut sections 109 and 111 by screws 119 and 121, respectively. The exposed outer end faces of the piston are worked to indicate the direction of rotation. The pistons 95 and 97 have inner pressure responsive faces 123 and 125, respectively. The faces 123 and 125 are separated from the sleeves 91 and 93, respectively, by gaps 126 and 128. The pistons 95 and 97 have outer faces 127 and 129, respectively, which are exposed in the chamber 63 and which are manually engageable to permit manual sliding movement of the valve element 67. The pistons 95 and 97 carry seals 131 and 133, respectively, each of which forms a substantially fluid-tight fit with the wall of the chamber 63.

The valve element 65 is movable between a forward position, i.e., the extreme downward position shown in FIG. 2, and a reverse position, i.e., an uppermost position with the driver 11 in the orientation shown in FIG. 2. In the forward position shown in FIG. 2, air at supply pressure from the supply port 81 flows through the inlet aperture 69 of the sleeve 65, the space 115, the passages 105 and 107, the passage sections 113, and the gap 126 to the conduit section 85. With the valve element 67 in the forward position shown in FIG. 2, the sleeve 93 closes off the inlet aperture 71 in the sleeve 65. Accordingly, air at supply pressure cannot flow to the conduit section 87. Rather, the valve element 67 provides communication between the conduit section 87 and the exhaust port 83. Specifically, air which has been exhausted from the air motor 21 passes through the conduit section 87, the gap 128, the passage sections 113, the passages 105 and 107, the space 117, and the exhaust aperture 79 to the exhaust port 83.

With the valve element 67 in the forward position shown in FIG. 2, air at supply pressure acts on the pressure responsive face 123 of the piston 95. Similarly, air at exhaust pressure acts on the pressure responsive face 125 of the piston 97. As the faces 123 and 125 are of substantially the same area, and because supply pressure greatly exceeds the exhaust pressure, the valve element 67 is releasably retained in the forward position by the air at supply pressure flowing to the air motor 21.

With the valve element 67 in the reverse position, the air at supply pressure is conducted from the supply port 81 to the conduit section 87. Under these circumstances air is exhausted from the conduit section 85 to the exhaust port 83.

The valve element 67 also has a null position which is axially intermediate the forward and reverse positions. In the null position, the wall section 103 is centered axially relative to the wall section 73. In this position, the sleeves 91 and 93 cover and close the inlet apertures 69 and 71, respectively. The sleeve 93 also closes the gap 128 in the null position. Accordingly, no air at supply pressure is allowed to pass to the air motor. Similarly, the wall section 103 covers and closes the exhaust apertures 79 so that no air flow from the air motor 21 to the exhaust port 83 is permitted.

The valve element 67 can be moved manually by pressing against the outer faces 127 and 129 of the pistons 95 and 97. For example, with the valve element 67 in the null position, the operator can push with his finger against the outer face 129 thereby moving the valve element downwardly toward the forward position. As soon as the valve element passes out of the null position toward the forward position, air at supply pressure acts on the pressure responsive face 123 thereby tending to automatically move the valve element the rest of the way to the forward position. Accordingly, air at supply pressure not only maintains the valve element 67 in the forward or reverse positions, but tends to move the valve element to these positions as soon as the valve element is moved past the null position.

The conduit section 85 extends from the control valve 61 downwardly through the handle 13 to the air motor 21 as shown in FIG. 1. The conduit section 87 extends to the air motor 21 in generally parallel relationship to the conduit section 85.

The exhaust port 83 (FIG. 2) is at one end of a passage 135 which leads from the reversing valve 61 to the bore 17 (FIG. 1). The exhaust air flows through the passage 135, the assembly 26, the upper one of the exhaust passages 37, and the exhaust passage 35 (FIG. 1). The air motor 21 may exhaust some air directly through the lower exhaust passage 37 and the exhaust passage 35.

A rotatable hollow shaft 137 (FIG. 1) is mounted in the barrel 15 by bearings 139 for rotation about an axis which extends generally transverse to the axis of the handle 13. The bearing 139 is held in position by retainers 141 and the bearing 139 is held in position by a bevel gear 143. The gear 143 is affixed to the hollow shaft 137 for rotation therewith by a key 145 and is held against axial movement by a retainer 147. The shaft 25 drives a bevel gear 149 which drives the gear 143 to thereby rotate the hollow shaft 137.

A member or tool such as an instrument 151 is mounted on the hollow shaft 137 for rotation therewith. The instrument 151 may be of various constructions and the one illustrated is purely illustrative. In the embodiment illustrated, the instrument 151 includes a head 153 and a shank 157. The head 153 is adapted to grip a wire 155. A major portion of the shank 157 is received within the hollow shaft 137. The shank 157 has a noncircular portion 159 which cooperates with a section of the hollow shaft 137 which is of complementary configuration to permit the hollow shaft to rotate the instrument 151. The head 153 releasably grips the wire 155 in a conventional manner so that the instrument can rotate the wire. The shank 157 is hollow to allow the wire 155 to pass therethrough. The wire 155 can be inserted through a tube 161 and into the shank 157.

The instrument 151 is releasably retained in the position shown in FIG. 1 by a detent 163 in the form of a ball. The detent 163 is radially movable in a radially extending port 165 in the hollow shaft 137 and seats in a circumferentially extending groove 167 formed adjacent the inner end of the shank 157. The detent 163 is held in locking relationship with the groove 167 by a retainer 169 which is slidable axially on the hollow shaft 137. The retainer 169 in the embodiment illustrated is in the form of a cylindrical sleeve and is biased by a spring 171 to a locking position in which it overlies the port 165 to prevent radial outward movement of the detent 163. The retainer 169 is movable axially to the left from the locking position shown in FIG. 1 to a releasing position shown in FIG. 7. In the releasing position the retainer 169 uncovers the port 165 and allows limited radial outward movement of the detent 163. The retainer 169 has a circumferentially extending groove 173 on the inner face thereof which allows such radial outward movement of the detent 163. A pin 174 in a slot connects the retainer 169 to the hollow shaft 137 so that these members rotate together.

Figure 7:
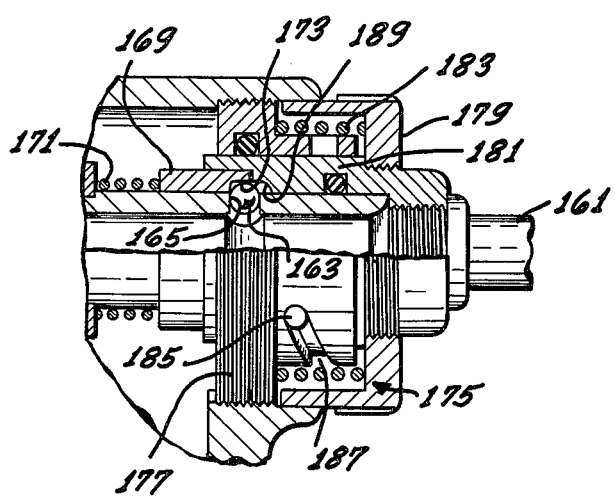
FIG. 7 is an enlarged fragmentary sectional view of the mechanism for releasably retaining the chuck with the detent being in a releasing position.

With the detent 163 allowed to move radially outwardly as shown in FIG. 7 to a releasing position, the instrument 151 can be easily removed from the driver 11 and replaced with a different instrument or other suitable rotatable member or tool.

Movement of the retainer 169 is controlled by an operating member 175. Specifically, a bushing 177 is threadedly attached to the barrel 15. The operating member 175 includes a knob 179 and an inner tubular section 181, which in the embodiment illustrated is threadedly attached to the knob 179. The inner tubular section 181 is mounted within the bushing 177 for axial and angular movement relative to the bushing. A spring 183 acts between the bushing 177 and the knob 179 to urge the operating member 175 axially to the right to the position shown in FIG. 1. A plurality of radially extending pins 185 (two being shown in FIG. 1) are mounted on and carried by the tubular section 181. The outer ends of the pins 185 project into helically extending slots 187, respectively, formed in the bushing 177.

When the operator grasps the knob 179 and moves the operating member 175 angularly, the pins 185 cooperate with the slots 187 in the bushing 177 to advance the operating member axially of the hollow shaft 137. This causes the tubular section 181 to engage the retainer 169 and move the latter axially to the left to the releasing position shown in FIG. 7. As indicated above, in the releasing position, the detent 163 can move radially outwardly to release the shank 157 of the instrument 151. The tubular section 181 has a groove 189 which cooperates with the groove 173 to permit such radial outward movement of the detent 163. Moreover, the surfaces defining the grooves 173 and 189 prevent escape of the detent 163. When the operator releases the knob 179, the spring 183 returns the operating member 175 to the position shown in FIG. 1.

The specific operation of the components of the driver 11 is described above. However, generally the operator would select the appropriate instrument 151 for the particular job to be carried out. The shank 157 is then inserted into the hollow shaft 137 with the operating member 175 in the releasing position shown in FIG.

7. When the shank 157 is fully inserted, the operating member is released to allow the spring 183 to return the operating member to the position shown in FIG. 1 and to allow the groove 173 to cam the detent 163 back to the locking position as shown in FIG. 1 in which it lockingly engages the groove 167. If the instrument 151 is for wire driving, a wire is then inserted into the free end of the tube 161, through the shank 157, and into the head 153. The head 153 is then tightened so that the wire will rotate with the instrument 151.

The operator then selects the direction of rotation, i.e., forward or reverse, by moving the valve element 67 (FIG. 2) to the appropriate position. The device 11 is then grasped by the handle 13 in a manner similar to the manner in which a handgun is held. The operating member 55 (FIG. 1) is operated by the index finger of the user to open the control valve 39. This initiates air flow to the air motor 21 to drive the air motor. The air motor in turn drives the wire 155.

Although an exemplary embodiment of the invention has been shown and described, many changes, modifications and substitutions may be made by one having ordinary skill in the art without necessarily departing from the spirit and scope of this invention.

I claim:

1. A driver for driving a surgical tool comprising:
a hand piece adapted to be held in the hand of a surgeon;
a barrel coupled to the hand piece and supporting a rotatable hollow shaft having a passage extending therethrough, the axis of said passage being generally transverse to the hand piece;
a reversible air motor mounted within said hand piece;
a drive shaft in said hand piece rotatably driven by said motor;
means interconnecting the drive shaft in driving relation to the hollow shaft;
said hollow shaft being adapted to receive and drive a surgical tool;
conduit means including first and second conduit sections for supplying air to the air motor to drive the air motor, the supply of air through the first conduit section to the air motor driving the air motor in a first direction and the supply of air through the second conduit section to the air motor driving the air motor in a second direction;
a reversing valve mounted on the hand piece, said reversing valve including a valve body having an inlet port connectible to air at supply pressure and an exhaust port for exhausting air at a pressure less than supply pressure;
said reversing valve providing a passage between supply air and said first conduit section in a first position and between supply air and said second conduit section in a second position, a valve element including an outer member and an inner member spaced from each other along at least a portion of the peripheries thereof to define an opening, said passage including said opening;
a chamber into which all of said ports and conduits open;
a sleeve fixed in said chamber of said valve body and having air passage means therein;
said valve element mounted for axial movement in said sleeve between said first position in which the valve element ports air from the inlet port to said first conduit section and from said second conduit section to said exhaust port and said second position in which the valve element ports air from the inlet port to said second conduit section and from said first conduit section to said exhaust port whereby the motor can be reversed by moving said valve element from one of said positions to the other of said positions;
said valve element being manually slidably movable between said positions thereof;
said valve element having first surface means against which air substantially at supply pressure can act when the valve element is in said first position to tend to hold the valve element in said first position;
said valve element having second surface means against which air substantially at supply pressure can act when the valve element is in said second position to tend to hold the valve element in said second position;
means in said hand piece to control the flow of air to said reversing valve;
detent means cooperating with said hollow member to receive and hold the shaft of a surgical tool; and
means located to the rear of said hollow member and cooperating with said detent to effect locking and release of the tool assembled to said driver.

2. A driver as defined in claim 1 wherein said valve element includes first and second pistons adjacent the opposite ends of said valve element, each of said pistons having an inner face, the inner faces of said first and second pistons comprising said first and second surface means, respectively.

3. A driver as defined in claim 2 wherein said chamber is open at the opposite ends thereof to expose said pistons, said pistons being manually engageable to permit movement of said valve element between said first and second positions thereof.

4. A driver as defined in claim 1 wherein said valve element has a null position in which the valve element is intermediate said first and second positions and in which it blocks flow to and from the first and second conduit sections, said first surface means cooperating with air at supply pressure to force the valve element toward the first position whenever the valve element is moved from said null position toward the first position, said second surface means cooperating with air at supply pressure to force the valve element toward the second position whenever the valve element is moved from said null position toward the second position.

5. A driver as defined in claim 1 wherein said valve element includes means defining an air passage, at least some of the air at supply pressure flowing from said inlet port through said air passage to said first conduit section when the valve element is in said first position, said means defining the air passage including a tubular member and a core within said tubular member, said core being spaced from at least a portion of said tubular member.

* * * * *